(12) United States Patent
van den Berg et al.

(10) Patent No.: US 9,592,966 B2
(45) Date of Patent: Mar. 14, 2017

(54) CONVEYOR SYSTEM COMPRISING A FRICTION COEFFICIENT MEASURING DEVICE

(71) Applicant: REXNORD FLATTOP EUROPE B.V., 's-Gravenzande (NL)

(72) Inventors: Rick Wilhelmus van den Berg, 's-Gravenzande (NL); Cornelis Hendrik Mijndert Menke, 's-Gravenzande (NL)

(73) Assignee: REXNORD FLATTOP EUROPE B.V., 'S-Gravenzande (NL)

( * ) Notice: Subject to any disclaimer, the term of this patent is extended or adjusted under 35 U.S.C. 154(b) by 0 days.

(21) Appl. No.: 14/910,441

(22) PCT Filed: Aug. 6, 2014

(86) PCT No.: PCT/NL2014/050551
§ 371 (c)(1),
(2) Date: Feb. 5, 2016

(87) PCT Pub. No.: WO2015/020524
PCT Pub. Date: Feb. 12, 2015

(65) Prior Publication Data
US 2016/0176648 A1     Jun. 23, 2016

(30) Foreign Application Priority Data

Aug. 7, 2013 (NL) ..................................... 2011275

(51) Int. Cl.
*B65G 47/22* (2006.01)
*B65G 45/02* (2006.01)
(Continued)

(52) U.S. Cl.
CPC ............. *B65G 45/02* (2013.01); *B65G 43/00* (2013.01); *B65G 45/10* (2013.01); *G01N 19/02* (2013.01)

(58) Field of Classification Search
CPC ........ B65G 45/02; B65G 45/04; B65G 45/08; G01N 19/02
(Continued)

(56) References Cited

U.S. PATENT DOCUMENTS 3,977,231 A     8/1976  Haehner et al.
4,262,776 A  *  4/1981  Wilson ................... B65G 45/02
                                                        137/93
(Continued)

FOREIGN PATENT DOCUMENTS

DE      33 40 457 A1     5/1985
WO      2010/063040 A2   6/2010

OTHER PUBLICATIONS

International Search Report under date of mailing of Nov. 13, 2014 in connection with PCT/NL2014/050551.

*Primary Examiner* — James R Bidwell
(74) *Attorney, Agent, or Firm* — Quarles & Brady LLP (57) ABSTRACT

In a conveyor system, a conveyor having a conveyor surface transports items. An optional lubricant dispensing device dispenses a lubricant composition on the conveyor surface. A friction coefficient measuring device measures a quantity proportional to the friction coefficient of the conveyor surface and provides a signal indicative for the measured quantity proportional to the friction coefficient. A control receives the signal indicative for the measured quantity. In one embodiment, the control provides a further signal when the measured quantity exceeds a threshold value or for regulating the lubricant amount to be dispensed based on the measured quantity in order to maintain the measured quan-
(Continued)

tity proportional to the friction coefficient within a predetermined range.

32 Claims, 5 Drawing Sheets (51) Int. Cl.
    *G01N 19/02* (2006.01)
    *B65G 43/00* (2006.01)
    *B65G 45/10* (2006.01)

(58) Field of Classification Search
    USPC .................................. 198/493, 500
    See application file for complete search history.

(56) References Cited

U.S. PATENT DOCUMENTS

| | | | | |
|---|---|---|---|---|
| 4,722,218 A | * | 2/1988 | Strader | G01N 19/02 |
| | | | | 73/9 |
| 6,189,686 B1 | * | 2/2001 | Shibayama | B65G 17/08 |
| | | | | 198/493 |
| 6,321,586 B1 | * | 11/2001 | Wojtowicz | G01N 3/56 |
| | | | | 73/9 |
| 6,742,625 B2 | * | 6/2004 | Rodemer | B65G 45/08 |
| | | | | 184/15.2 |
| 2002/0062678 A1 | | 5/2002 | Ahn et al. | |
| 2003/0207040 A1 | * | 11/2003 | Bennett | B65G 45/02 |
| | | | | 198/500 |
| 2007/0119685 A1 | * | 5/2007 | Divisi | B65G 45/02 |
| | | | | 198/493 |

\* cited by examiner

CONVEYOR SYSTEM COMPRISING A FRICTION COEFFICIENT MEASURING DEVICE

CROSS-REFERENCE TO RELATED APPLICATIONS

This application represents the national stage entry of PCT International Application No. PCT/NL2014/050551 filed Aug. 6, 2014, which claims the benefit of Netherlands Patent Application 2011275 filed Aug. 7, 2013, both of which are hereby incorporated herein by reference for all purposes.

STATEMENT REGARDING FEDERALLY SPONSORED RESEARCH OR DEVELOPMENT

Not applicable.

FIELD OF THE INVENTION

The invention relates to a conveyor and lubricating system, said system including: a conveyor having a conveyor surface, said conveyor being arranged for transporting items on the conveyor surface along a conveyor path; a lubricant dispensing device for dispensing a lubricant composition on the conveyor surface; a friction coefficient measuring device for measuring a quantity proportional to the friction coefficient of said conveyor surface and for providing a signal indicative for said measured quantity proportional to the friction coefficient, said friction coefficient measuring device comprising a contact portion for contacting the conveyor surface; and a control means for controlling said lubricant dispensing device, said measuring device being operatively connectable to said control means for supplying said signal indicative for said measured quantity proportional to the friction coefficient to said control means, said control means being arranged for controlling the lubricating dispensing device for regulating the lubricant amount to be dispensed in order to maintain the measured quantity proportional to the friction coefficient within a predetermined range.

BACKGROUND OF THE INVENTION

Such a conveyor and lubricating system is e.g. known from EP-A-1790968. With the known system items, such as plastic bottles, glass bottles, cans and cartons can be transported along a conveyor path on a conveyor surface of a conveyor. The conveyor can be provided at its end with collection units which channel the items towards subsequent treatments (for example to feed them to a labeling machine). In particular, the collection units comprise guides defining a passage enabling only one item to pass; hence in practice the items can arrive continuously and are accumulated at the guides, whereas only one item at a time can pass through the port and be transported to a next station. To facilitate sliding and to prevent the items from falling over because of friction, the conveyor upper surface on which the items are placed is lubricated by means of a lubricant dispensing device.

In EP-A-1790968 it is stated that the lubrication of the conveyor can be automatically regulated by adapting it to the continuous changes in the friction conditions between the conveyor surface and the items. In this manner the conveyor surface can always be lubricated correctly and it can be prevented on the one hand that lubrication is applied excessively which could lead to spillage on the floor leading to dangerous situations for personnel and on the other hand it can be prevented that lubrication is applied insufficiently in which latter case the items (on being braked and accumulated at the crosspieces) could overturn. To realize such an automatic regulation EP-A-1790968 discloses a friction coefficient measuring device comprising a slider connected via a spring to a sensor able to measure the force acting. The slider is provided with a contact portion slidably associated with the conveyor surface. During operation, the conveyor moves in a conveying direction and the slider—which supports the contact portion slidably associated with the conveyor—is urged in a direction opposite the conveying direction. Consequently the spring is pulled, which deforms by lengthening; which latter exerts a force on the sensor which is proportional to the friction between the conveyor surface and the contact portion which is dependent on the amount of lubricant present on the conveyor surface.

The quantity measured by the sensor is compared with a reference range for this quantity, to evaluate whether it lies or does not lie within this range, and the lubricant dispensing device is regulated or controlled for dispensing a lubricant composition on the conveyor surface depending on the result of the comparison. Although the known system seems to enable the lubricant amount to be dispensed onto the conveyor automatically controlled and regulated on the basis of the instantaneous operating conditions it appears in praxis that during use of the conveyor, in particular after extended time periods of use, items transported on the conveyor can overturn and are not able to overcome even small inclinations, which problems are an indication that the applied lubricant amount is not sufficient to maintain the friction coefficient within the predetermined range. Furthermore, it has appeared that when a different kind of items are to be transported by the conveyor, which different kind of items can e.g. have a different center of gravity, a different weight, a different contact area with the conveyor etc. than the items transported previously, the problems mentioned above—i.e. excessive or insufficient amount of lubricant dispensed on conveyor surface—increase. To overcome these problems the whole system needs to be recalibrated leading to undesired downtime of the system.

In WO-2010/063040 another system for controlling the amount of lubricant to be dispensed on a conveyor is disclosed, which system comprises a small enclosure which is in the nature of a cage in which a selected number of items, e.g. two items, are held captive. The items rest on an upper surface of a conveyor and, when the conveyor is moved in normal operation, the items are held in position with the conveyor sliding below. The enclosure is linked via an intermediate strain gauge to an anchor which is attached to a fixed structure. A signal which is produced by the strain gauge is applied to a control unit operatively connected to a lubricant applicator which applies lubricant onto the upper surface of the conveyor at a desired value. The signal is thus dependent on the magnitude of a force generated between the strain gauge and the anchor upon movement of the conveyor, which force is proportional to the friction between the items and the upper surface of the conveyor. Although in this system the actual friction or coefficient of friction between an item and a conveyor surface is measured on the basis of the instantaneous operating conditions and used for applying lubricant in a desired amount to the conveyor surface the use of the small enclosure holding the measuring items seriously interferes with the 'normal' transport of items on the conveyor along a conveyor path which leads to a reduction of the throughput time. In addition, it has appeared in practice that although the measurements are based the instantaneous operating conditions that in some cases items such as bottles transported on the conveyor can overturn and are not able to overcome even small inclinations.

SUMMARY OF THE INVENTION

It is an object of the invention to provide a conveyor system including a conveyor having a conveyor surface, said conveyor being arranged for transporting items along a conveyor path on the conveyor surface; a friction coefficient measuring device for measuring a quantity proportional to the friction coefficient of said conveyor surface and for providing a signal indicative for said measured quantity proportional to the friction coefficient, said friction coefficient measuring device comprising a contact portion for contacting the conveyor surface; and a control means operatively connectable to said measuring device for receiving said signal indicative for said measured quantity proportional to the friction coefficient, said control means being arranged for providing a further signal in dependence of said signal indicative for said measured quantity proportional to the friction coefficient, in which the measured quantity proportional to the friction coefficient provides a more reliably indication of the friction coefficient.

It is a further object of the invention to provide a conveyor and lubricating system in which the amount of lubricant can be applied more correctly to the surface of a conveyor over an extended period of time. These objects are in accordance with the invention obtained by a conveyor and lubricating system, said system including: a conveyor having a conveyor surface, said conveyor being arranged for transporting items along a conveyor path on the conveyor surface; a lubricant dispensing device for dispensing a lubricant composition on the conveyor surface; a friction coefficient measuring device for measuring a quantity proportional to the friction coefficient of said conveyor surface and for providing a signal indicative for said measured quantity proportional to the friction coefficient, said friction coefficient measuring device comprising a contact portion for contacting the conveyor surface; and a control means for controlling said lubricant dispensing device, said measuring device being operatively connectable to said control means for supplying said signal indicative for said measured quantity proportional to the friction coefficient to said control means being arranged for controlling the lubricating dispensing device for regulating the lubricant amount to be dispensed in order to maintain the measured quantity proportional to the friction coefficient within a predetermined range, characterized in that the friction coefficient measuring device comprises a replacement device for automatically replacing the contact portion of the friction coefficient measuring device.

The invention is based on the insight that the problems that arise during use of the system known from EP-A-1790968 are based on the fact that the measured quantity proportional to the friction coefficient is strongly dependent on the properties of the surface of the contact portion. This surface can in time collect more and more lubricant or other contaminations from the conveyor surface which negatively influences the measured quantity which then is not proportional anymore to the friction coefficient of the conveyor surface. By in accordance with the invention using a replacement device for automatically replacing the contact portion of the friction coefficient measuring device it is possible to replace a used contact portion by a new contact portion having the same properties, thus leading to a more representative measurement of the friction coefficient of the conveyor surface which can provide reliable measured quantities over an extended period of time for dispensing desired amounts of lubricant onto the conveyor surface.

In a further aspect of the invention a conveyor system is provided, said conveyor system including: a conveyor having a conveyor surface, said conveyor being arranged for transporting items along a conveyor path on the conveyor surface; a friction coefficient measuring device for measuring a quantity proportional to the friction coefficient of said conveyor surface and for providing a signal indicative for said measured quantity proportional to the friction coefficient, said friction coefficient measuring device comprising a contact portion for contacting the conveyor surface; and a control means operatively connectable to said measuring device for receiving said signal indicative for said measured quantity proportional to the friction coefficient, said control means being arranged for providing a further signal in dependence of said signal indicative for said measured quantity proportional to the friction coefficient; characterized in that the friction coefficient measuring device comprises a replacement device for automatically replacing the contact portion of the friction coefficient measuring device, and in that the control means are arranged for comparing said measured quantity proportional to the friction coefficient indicated by said signal indicative for said measured quantity with a threshold value and for providing said further signal when said measured quantity equals to or exceeds said threshold value. This aspect of the invention is based on the insight that the friction coefficient measurement device can also be used in a conveyor system without a lubricant dispensing device. In such a conveyor system the further signal generated by the control means indicates in accordance with the present invention that the measured quantity proportional to the friction coefficient exceeds a threshold value, which further signal can be used as an indication that the conveyor surface needs to be cleaned.

Preferably the friction coefficient measuring device comprises a control unit for controlling functions and programmable operations of the friction coefficient measuring device, such that replacement of the contact portion can be performed automatically. In an embodiment of a conveyor system according to the invention the control unit controls the replacement device for periodically replacing a contact portion. Alternatively or in addition the control unit can control the replacement device for replacing a contact portion each time new items are to be transported by said conveyor.

In an advantageous embodiment of a conveyor system according to the invention the contact portion is movably mounted relative to the conveyor surface. The control unit is then arranged for controlling the friction coefficient measuring device for moving a contact portion into contact with the conveyor surface for measuring a quantity proportional to the friction coefficient of said conveyor surface during measuring periods which is shorter than a transport period in which the conveyor transport items and for moving the contact portion out of contact with the conveyor surface outside the measuring period. In this manner the contact portion is brought into contact with the conveyor surface only during the actual measurement. It is then preferred when the control unit controls the replacement device for replacing the contact portion outside the measuring periods, in particular the control unit controls the replacement device for replacing the contact portion each time after a measuring period has ended.

A conveyor system according to the invention can be constructed in a simple manner when a contact portion is formed by a separate disposable contact piece. In case the friction coefficient measuring device comprises a discharge conveyor for discharging a contact piece to a waste container used contact pieces can be discharge automatically to the waste container. Such a separate disposable contact piece can be a pad or a cushion. Alternatively the contact portion can be formed by a separate reusable contact piece. In this regard it is advantageous that the contact piece is formed by an item which is to be transported on the conveyor.

In an advantageous embodiment of a conveyor system according to the invention the contact portion of the friction coefficient measuring device comprises a foil supplying device for supplying a contact foil and an engagement pad for bringing the contact foil into engagement with the conveyor surface, said foil supplying device being arranged for supplying contact foil in between the engagement pad and the conveyor surface. In this manner the replacement device can be arranged for replacing the contact foil between the engagement pad and the conveyor surface, e.g. in case the foil is wound on a rotatable storage roll by unwinding the foil such that an unused portion of the foil is supplied between the engagement pad and the conveyor surface.

A conveyor system according to the invention can be constructed in a compact manner when the friction coefficient measuring device comprises a displaceable magazine containing a plurality of separate contact portions, said magazine being displaceable relative to the conveyor surface for allowing one contact portion of said plurality of contact portions to be movable relative to the conveyor surface for contacting the conveyor surface. Measurements of the friction coefficient can then be done within a short interval after each other when the control unit controls the displaceable magazine for moving said one contact portion of the plurality of contact portions out of contact with the conveyor surface after a measuring period has ended and for allowing another contact portion of said plurality of contact portions to be movable relative to the conveyor surface for contacting the conveyor surface.

In a further embodiment of a conveyor system according to the invention the friction coefficient measuring device comprises a cleaning device for cleaning the contact portion. In this manner previously applied lubricant or other contaminations can be removed from the contact portion and thus can not influence future measurements in a negative way. In this manner it is also possible to arrange the cleaning device for cleaning a used contact piece for making the contact piece suitable for reuse. In addition or alternatively the cleaning device can clean the contact portion before each measurement, as a result of which the number of times a contact portions needs to be replaced can be reduced. In this manner the problems arising in the system known from HP-A-1790968 can be overcome alternatively by regularly cleaning the contact portion to obtain reproducible measuring quantities.

Consequently the invention also relates to a conveyor system, said system including: a conveyor having a conveyor surface, said conveyor being arranged for transporting items along a conveyor path on the conveyor surface; an optional lubricant dispensing device for dispensing a lubricant composition on the conveyor surface; a friction coefficient measuring device for measuring a quantity proportional to the friction coefficient of said conveyor surface and for providing a signal indicative for said measured quantity proportional to the friction coefficient, said friction coefficient measuring device comprising a contact portion for contacting the conveyor surface; and a control means, operatively connectable to said measuring device for supplying said signal indicative for said measured quantity proportional to the friction coefficient to said control means, said control means optionally being arranged for controlling the lubricating dispensing device for regulating the lubricant amount to be dispensed in order to maintain the measured quantity proportional to the friction coefficient within a predetermined range; characterized in that the friction coefficient measuring device comprises a cleaning device for cleaning the contact portion.

In a still further embodiment of a conveyor system according to the invention in which said conveyor is arranged for transporting items having a base surface contacting the conveyor surface along a conveyor path; said system further includes an item base surface friction coefficient measuring device for measuring a quantity proportional to the friction coefficient of said item base surface and for providing a signal indicative for said measured quantity proportional to the item base surface friction coefficient to said control means, said item base surface friction coefficient measuring device comprising an item holder and an item base surface contact portion for contacting the base surface of an item, said item base surface friction measuring device being operatively connectable to said control means for supplying said signal indicative for said measured quantity proportional to the item base surface friction coefficient to said control means, and said control means being arranged for comparing said measured quantity proportional to the friction coefficient indicated by said signal indicative for said measured quantity with a threshold value and for providing said further signal when said measured quantity equals to or exceeds said threshold value taking the measured quantity proportional to the item base surface friction coefficient into account or said control means being optionally arranged for controlling the lubricating dispensing device for regulating the lubricant amount to be dispensed taking the measured quantity proportional to the item base surface friction coefficient into account.

This beneficial aspect of the invention is based on the insight that the problems arising in the system known from EP-A-1790968 are at least partly the result thereof that the contribution to the friction coefficient of the item itself, in particular of the item base surface which contacts the conveyor surface, is not taken into account when determining the friction coefficient between the items and the conveyor surface. By in accordance with this aspect of the invention separately measuring the item base surface friction coefficient and optionally regulating the lubricant amount to be dispensed on the conveyor surface while taking the measured quantity proportional to the item base surface friction coefficient into account, the amount of lubricant to be applied to the conveyor surface can be determined more correctly which can lead to a more correct operation of the system.

In a specific aspect of a conveyor system according to the invention the item base surface friction coefficient measuring device is arranged for picking up an item transported along the conveyor path on the conveyor surface and is arranged for measuring a quantity proportional to the friction coefficient of a base surface of an item picked up from the conveyor surface. In this manner representative items to be used for measuring the item base friction coefficient can be taken out of the conveyor path and thus do not interfere with the 'normal' operation of transport of the other items along the conveyor path on the conveyor in which manner the problems arising in the system known from WO-A-

2010/063040 can be overcome. It is then preferred that the item base surface friction coefficient measuring device is arranged for positioning an item back in the conveyor path on the conveyor surface after the item base surface friction coefficient measuring device has performed an item base surface friction coefficient measurement on said item. Furthermore, this aspect of the invention is based on the insight that capturing items in an enclosure while the items are still present on the conveyor surface, negatively influences the distribution of lubricant on the conveyor surface since holding forces of the cage on the items within the enclosure lead to the items exerting forces on the lubricant on the conveyor surface in an uncontrolled manner. Thereby the distribution of the lubricant on the conveyor surface can be altered which can lead to an uncontrollable friction coefficient between the other items transported along the conveyor path on the conveyor and the conveyor surface. By in accordance with this aspect of the invention picking up items which are used for performing measurements from the conveyor surface this problem is avoided.

Additionally or alternatively this problem can be overcome in a further embodiment of a conveyor system according to the invention wherein the item base surface contact portion for contacting the base surface of an item comprises a measuring conveyor track having a measuring conveyor track surface for supporting an item, said measuring conveyor track surface being different from the conveyor path. By using a measuring conveyor track surface which is different from the conveyor path the measuring conveyor track surface is only used to support items of which the item base surface friction coefficient is measured and is not used for transporting other items. In particular the item base surface friction coefficient measuring device comprises an item base surface control unit for controlling functions and programmable operations of the item base surface friction coefficient measuring device so that the operation of the item base surface friction coefficient measuring device can be effected automatically.

Although an item base surface friction coefficient measuring device which is arranged for picking up an item transported along the conveyor path on the conveyor surface the item base surface friction coefficient measuring device can be used for placing an item on the measuring conveyor track surface a simple and compact embodiment of a conveyor system according to the invention can be obtained when the item base surface friction coefficient measuring device comprises a first switch for diverting an item from the conveyor path to the measuring conveyor track. In order to bring the item of which the item base surface friction coefficient has been measured back into the conveyor path in a simple manner the item base surface friction coefficient measuring device comprises a second switch for conveying an item from the measuring conveyor track back in the conveyor path.

In an embodiment of a conveyor system according to the invention the measuring conveyor track is formed by a measuring conveyor separate from the conveyor for transporting items, wherein preferably the measuring conveyor track surface is formed of the same material as the conveyor surface. Please note that the surfaces can be different from each other and in that case a conversion factor needs to be determined, preferably initially, which conversion factor can be used to transform the friction coefficient of the measuring conveyor track surface into the friction coefficient of the conveyor surface.

In an alternative, compact embodiment of a conveyor system according to the invention the measuring conveyor track is formed by an isolated portion of the conveyor surface of the conveyor on which the items are transported, meaning that this measuring conveyor track is not part of the conveyor path between the guides. A simple construction of a conveyor system can then be realized when the measuring conveyor track is positioned near an S-shaped transfer bend of the conveyor for transporting items.

In an embodiment of a conveyor system according to the invention which can be easily implemented the conveyor is an endless conveyor having an upper conveyor surface on which items are to be transported and a returning conveyor surface, which is identical to the upper conveyor surface but directed downwards, the measuring conveyor track being formed by the returning conveyor surface.

To be able to obtain reproducible measurements over an extended period of time the item base surface friction coefficient measuring device comprises a measuring conveyor cleaning device for cleaning the measuring conveyor track surface. In this manner previously applied lubricant or other contaminations can be removed from the measuring conveyor track surface and thus can not influence future measurements in a negative way.

In a preferred embodiment of a conveyor system according to the invention the item base surface friction coefficient measuring device comprises a weighing device for weighing an item of which the item base surface friction coefficient is to be measured, said weighing device being operationally connectable to said control unit. By determining the weight of an item, which weight is contributory to the friction, it is possible to use the system for transporting items of different weights while still being able to e.g. regulate the amount of lubricant to be dispensed in an automatic manner.

In another embodiment of a conveyor system according to the invention the item base surface friction coefficient measuring device comprises an image obtaining and processing device for obtaining an image of an item of which the item base surface friction coefficient is to be measured and for processing said obtained image, said image obtaining and processing device being operationally connectable to said control unit. In this manner it is possible to determine or at least estimate the position of the center of gravity of an item to be transported with regard to the conveyor surface which position is contributory to the operation of the system and the amount of lubricant to be dispensed in case a lubricant dispensing device is present. For example, an item having a center of gravity at a large distance from the conveyor surface has a greater tendency to overturn than an item of which the center of gravity is positioned close to the conveyor surface.

In an embodiment of a conveyor system according to the invention the item base surface friction coefficient measuring device then comprises an item base surface contact portion replacement device for automatically replacing the item base surface contact portion of the item base surface friction coefficient measuring device, preferably for replacing the item base surface contact portion after each item base surface friction coefficient measurement so that it is possible to obtain reproducible and correct measurement in the course of operational use of the conveyor. In this manner the item base surface contact portion can e.g. be formed by a rotating disc or a stationary disc on which the item is rotated. The item base surface friction coefficient can then e.g. be determined by comparing the moments or forces necessary for effecting the rotation with and without contact. The item base surface control unit can control the item base surface contact portion replacement device for periodically replacing an item base surface contact portion, preferably for replacing an item base surface contact portion each time the item base surface friction coefficient of another item is to be measured.

In an embodiment of a conveyor system according to the invention the item base surface contact portion can be movably mounted relative to the item base surface, wherein the item base surface control unit controls the item base surface friction coefficient measuring device for moving an item base surface contact portion into contact with the item base surface for measuring a quantity proportional to the friction coefficient of said item base surface.

A conveyor system according to the invention can be constructed in a simple manner when an item base surface contact portion is formed by a separate disposable item base surface contact piece. In case the item base surface friction coefficient measuring device comprises a discharge conveyor for discharging an item base surface contact piece to a waste container used item base surface contact pieces can be discharge automatically to the waste container.

A conveyor system according to the invention can be constructed in a compact manner when the item base surface friction coefficient measuring device comprises a displaceable magazine containing a plurality of separate item base surface contact portions, said magazine being displaceable relative to an item base surface for allowing one item base surface contact portion of said plurality of item base surface contact portions to be movable relative to an item base surface for contacting an item base surface. Measurements of the item base surface friction coefficient can then be done within a short interval after each other when the control unit controls the displaceable magazine for moving said one item base surface contact portion of the plurality of item base surface contact portions out of contact with the item base surface after an item base surface friction coefficient measurement has been performed and for allowing another item base surface contact portion of said plurality of item base surface contact portions to be movable relative to the item base surface for contacting the item base surface of another item.

In a further embodiment of a conveyor system according to the invention the item base surface friction coefficient measuring device comprises a cleaning device for cleaning an item base surface contact portion. In this manner previously applied lubricant or other contaminations can be removed from the item base surface contact portion and thus can not influence future measurements in a negative way. It is then possible to arrange the cleaning device for cleaning an item base surface contact piece for making the item base surface contact piece suitable for reuse. Alternatively or on addition the number of times an item base surface contact portion needs to be replaced can be reduced.

Although the invention is applicable to all kinds of conveyors the invention is in particular advantageous when the conveyor used is a modular conveyor. Modular conveyors are often used when the conveyor path comprises bends, and in particular at such bends it is extremely important to lubricate the surface bends correctly to prevent items from tumbling over. This can in accordance with the invention be realized by controlling a present lubricant dispensing device by the control means based on the signal indicative for the measured quantity proportional to the friction coefficient or to take appropriate actions, such as cleaning the conveyor surface, in case the measured quantity proportional to the friction coefficient exceeds a threshold value. Consequently the invention in particular relates a conveyor system, in which said system includes: a modular conveyor having a modular conveyor surface, said conveyor being arranged for transporting items along a conveyor path on the modular conveyor surface in a conveyance direction; an optional lubricant dispensing device for dispensing a lubricant composition on the modular conveyor surface; and a friction coefficient measuring device for measuring a quantity proportional to the friction coefficient of said modular conveyor surface and for providing a signal indicative for said measured quantity proportional to the friction coefficient, said friction coefficient measuring device comprising a contact portion for contacting the modular conveyor surface; and a control means operatively connectable to said measuring device for supplying said signal indicative for said measured quantity proportional to the friction coefficient to said control means, said control means being optionally arranged for controlling the lubricating dispensing device for regulating the lubricant amount to be dispensed in order to maintain the measured quantity proportional to the friction coefficient within a predetermined range or being arranged for comparing said measured quantity proportional to the friction coefficient indicated by said signal indicative for said measured quantity with a threshold value and for providing said further signal when said measured quantity equals to or exceeds said threshold value.

In an embodiment the modular conveyor comprises a number of modular conveyor components which are positioned adjacent to each other in a direction substantially transverse to the conveyance direction, wherein the conveyor path runs over at least two modular conveyor components of said number of modular conveyor components. In particular with such a modular conveyor with a number of adjacent modular conveyor components where the items pass from one of the modular conveyor component to an adjacent modular conveyor component it is important to properly clean the conveyor surface or to adjust the amount of lubricant provided on the modular conveyor surface to ensure that the items pass from one modular conveyor component to another modular conveyor component correctly. Preferably, the system comprises a separate friction coefficient measuring device for each of the modular conveyor components for measuring a quantity proportional to the friction coefficient of the surface of a respective modular conveyor component and for providing a signal indicative for said measured quantity proportional to the friction coefficient, each of said friction coefficient measuring devices comprising a contact portion for contacting the surface of the respective modular conveyor component. It is then preferred that at least one but preferably all of the friction coefficient measuring devices comprise a replacement device for automatically replacing the contact portion of the friction coefficient measuring device. For redundancy reasons, respective preferred features of the system comprising modular conveyors are not mentioned in the following in detail. However, reference is made to the before-mentioned, wherein all features mentioned as to be relevant or advantageous with regard to a system with a conveyor in general are transferable to the friction coefficient measuring device for measuring the friction coefficient component of modular conveyors, wherein all possible combinations of features as disclosed above are also applicable to the system with a modular conveyor.

The invention in addition relates to a method of dispensing a lubricant composition on a conveyor surface of a conveyor of a conveyor and lubricating system, wherein the method comprises the steps of: transporting items along a conveyor path on the conveyor surface; dispensing a lubricant composition on the conveyor surface; measuring a quantity proportional to the friction coefficient of said conveyor surface and providing a signal indicative for said measured quantity proportional to the friction coefficient, said friction coefficient measuring device comprising a contact portion, said contact portion being brought into contact with the conveyor surface for measuring the quantity; and regulating the lubricant amount to be dispensed based on the measured quantity in order to maintain the measured quantity proportional to the friction coefficient within a predetermined range. As mentioned above the method is in particular useful when the conveyor is a modular conveyor, preferably comprising a number of adjacent modular conveyor components. Preferably the method comprises the step of replacing, preferably automatically replacing the contact portion of the friction coefficient measuring device. In an embodiment of a method according to the invention the contact portion is replaced periodically. In addition or alternatively a contact is replaced portion each time new items are to be transported by said conveyor.

In an advantageous embodiment of a method in accordance with the invention the measurement is performed within a measuring period and the contact portion is replaced each time after a measuring period has ended. Preferably the method comprises the step of cleaning the contact portion, in particular for making the contact portion suitable for reuse. It can be advantageous when the method further comprises the step of measuring the item base surface friction coefficient, preferably with an item base surface friction coefficient measuring device as described above. For redundancy reasons, further respective features of the method for measuring the friction coefficient are not mentioned in the following in detail. However, reference is made to the before-mentioned, wherein all features mentioned as to be relevant or advantageous with regard to the system are transferable to the method, such as for example that in the method as contact piece an item to be transported can be used.

The invention in addition relates to a method for cleaning a conveyor surface of a conveyor, wherein the method comprises the steps of: transporting items along a conveyor path on the conveyor surface; measuring a quantity proportional to the friction coefficient of said conveyor surface and providing a signal indicative for said measured quantity proportional to the friction coefficient, said friction coefficient measuring device comprising a contact portion, said contact portion being brought into contact with the conveyor surface for measuring the quantity; and providing a further signal when the measured quantity proportional to the friction coefficient exceeds a threshold value, said further signal being used for initiating cleaning of the conveyor surface.

The invention further relates to a friction coefficient measuring device for use in a system according to the invention, said friction coefficient measuring device being arranged for measuring a quantity proportional to the friction coefficient of a conveyor surface and for providing a signal indicative for said measured quantity proportional to the friction coefficient, said friction coefficient measuring device comprising a contact portion for contacting a conveyor surface, characterized in that the friction coefficient measuring device comprises a replacement device for automatically replacing the contact portion of the friction coefficient measuring device.

For redundancy reasons, the respective features of the friction coefficient measuring device are not mentioned in the following in detail. However, reference is made to the before-mentioned, wherein all features mentioned as to be relevant or advantageous with regard to the system are transferable to the friction coefficient measuring device.

The invention still further relates to an item base surface friction coefficient measuring device for use in a system according to the invention, said item base surface friction coefficient measuring device being arranged for measuring a quantity proportional to the item base surface friction coefficient of a base surface of an item and for providing a signal indicative for said measured quantity proportional to the item base surface friction coefficient, said item base surface friction coefficient measuring device comprising an item holder and an item base surface contact portion for contacting the base surface of an item. The invention also relates to an item base surface friction coefficient measuring device for use in a conveyor and lubricating system without a friction coefficient measuring device for measuring a quantity proportional to the friction coefficient of said conveyor surface and for providing a signal indicative for said measured quantity proportional to the friction coefficient, said item base surface friction coefficient measuring device being arranged for measuring a quantity proportional to the item base surface friction coefficient of a base surface of an item and for providing a signal indicative for said measured quantity proportional to the item base surface friction coefficient, said item base surface friction coefficient measuring device comprising an item holder and an item base surface contact portion for contacting the base surface of an item.

For redundancy reasons, the respective features of the item base surface friction coefficient measuring device are not mentioned in the following in detail. However, reference is made to the before-mentioned, wherein all features mentioned as to be relevant or advantageous with regard to the system are transferable to the item base surface friction coefficient measuring device.

These and other objects and advantages of the invention will become more apparent from the following detailed description of an exemplary embodiment of a conveyor and lubricating system according to the invention taken in conjunction with the accompanying drawings.

DETAILED DESCRIPTION OF THE EXAMPLE EMBODIMENTS

Please note that the invention will be described by way of example with reference to a conveyor and lubricating system, but it is noted that the invention can also be used in a conveyor system without a lubricant dispensing device. In such a conveyor system the control means are arranged for providing a further signal in dependence of a signal indicative for said measured quantity proportional to the friction coefficient provided by a friction measuring device. The further signal is generated by the control means when the measured quantity proportional to the friction coefficient exceeds a threshold value, which further signal e.g. can be used as an indication that the conveyor surface needs to be cleaned.

Figure 1:
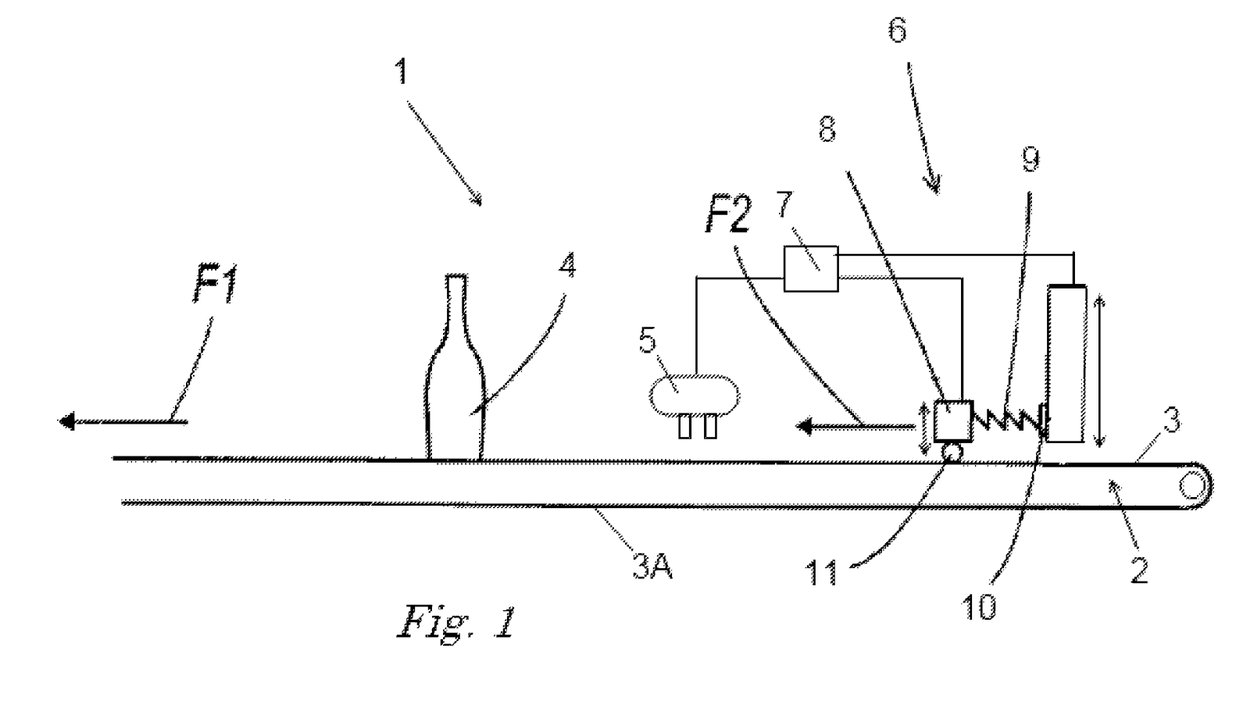
FIG. 1 very schematically shows an embodiment of a conveyor and lubricating system according to the invention.

An embodiment of a conveyor and lubricating system 1 according to the invention is shown schematically in FIG. 1. The system 1 includes an endless conveyor 2 having an upper conveyor surface 3 on which items 4, in this example bottles, are transported. The system 1 further comprises a lubricant dispensing device 5 for dispensing a lubricant composition on the conveyor surface 3. For measuring a quantity proportional to the friction coefficient of said conveyor surface 3 a friction coefficient measuring device 6 is provided which provides a signal indicative for said measured quantity proportional to the friction coefficient to a control, such as a control unit 7, to which it is operatively connected. Said control unit 7 controls the lubricant dispensing device 5 based on the signal received such that the lubricating dispensing device 5 is regulated for dispensing a lubricant amount in order to maintain the measured quantity proportional to the friction coefficient within a predetermined range. To maintain the quantity of lubricant within a predetermined range is not only important for correct transport of the items 4 but is also important for preventing soiling of the floor on which the conveyor is placed. Since the conveyor 2 is endless it has a lower or returning conveyor surface 3A, which is identical to the upper conveyor surface but directed downwards, and in case excess of lubricant is present thereon it can unwantedly drip on the floor and also to prevent this from happening the quantity of lubricant has to be maintained within a predetermined range.

The friction coefficient measuring device 6 comprises in this embodiment a slider 8 connected via elastic means 9 (such as a spiral spring) to a sensor 10 able to measure the force acting on it and provided with a contact portion 11 which is slidably associated with the conveyor 2. During operation, the conveyor 2 moves as indicated by the arrow F1. The slider 8 which supports the contact portion 11 is urged as indicated by the arrow F2 and consequently pulls the spring 9, which deforms by lengthening; this latter exerts a force on the sensor 10 indicative of the force F2 and hence proportional to the friction between the conveyor 2 and the contact portion 13 which depends on the amount of lubricant applied on the conveyor surface 3. Please note, that although this embodiment is described with reference to a slider 8 it is in accordance with other embodiments of the invention also possible to additionally press the contact portion with a predetermined force on the conveyor surface.

The contact portion 11 is movably mounted relative to the conveyor surface 3 as is indicated by the double headed arrows, which movement is controlled by a control unit for controlling functions and programmable operations of the friction coefficient measuring device, which control unit—in this embodiment—is formed by the control means which also controls the functioning of the lubricant dispensing device 5, but which control unit in other embodiments can be formed by a separate control unit. The control unit 7 controls the friction coefficient measuring device 6 for moving the contact portion 11 into contact with the conveyor surface 3 during measuring periods for measuring a quantity proportional to the friction coefficient of said conveyor surface 3. The measuring periods are short relative to the transport period in which the conveyor 2 transports the bottles 4. For example, a measuring period can amount to about 60 seconds. Outside the measuring periods the control unit 7 moves the contact portion 11 out of contact with the conveyor surface 3.

In accordance with the invention the friction coefficient measuring device 6 comprises a replacement device for automatically replacing the contact portion 11 of the friction coefficient measuring device 6, wherein the replacement device is controlled by the control unit 7 for periodically replacing a contact portion 11. The control unit 7 can be programmed to replace a contact portion 11 at regular intervals, but in the present embodiment at least each time new items 4 are to be transported by said conveyor 2. In this regard new item are to be interpreted as items having a weight, a size, a shape or which are made of a different material which is different from items which were transported previously. In the shown embodiment replacing a contact portion 11 takes place under control of the control unit 7 outside the measuring periods and preferably each time after a measuring period has ended.

Figure 2:
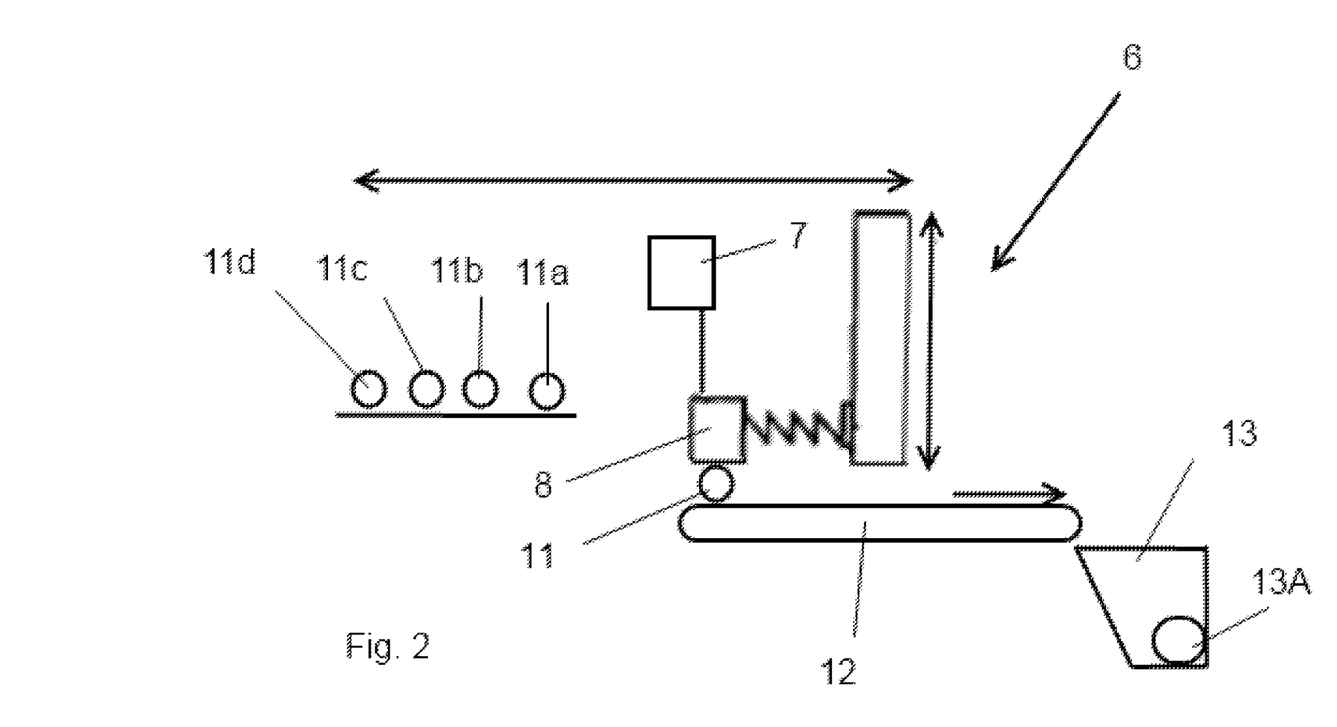
FIG. 2 very schematically shows an embodiment of a contact portion replacement device used in a system of FIG. 1.

In FIG. 2 an embodiment of a replacement device according to the invention is shown schematically. In this embodiment a contact portion 11 is formed by a separate disposable contact piece 11 which is removably attached to the slider 8, which—under control of the control unit 7—functions as replacement device. The slider 8 can e.g. be equipped with a gripper for gripping a disposable contact piece 11, which gripper can be a mechanical gripper or e.g. an electromagnetical gripper. In order to replace a contact piece 11 the friction coefficient measuring device 6 is operated to lift the contact piece 11 out of contact with the conveyor surface 3 and is as a whole displaced to above a discharge conveyor 12. The gripper of the slider 8 is operated to release the contact piece 11 which is dropped on the discharge conveyor 12 and discharged to a waste container 13. Thereafter the friction coefficient measuring device 6 is—under control of the control unit 7—displaced to a storage or magazine of contact pieces 11a-11d and the gripper of the slider 8 is operated such as to grip a new contact piece, e.g. contact piece 11a after which the friction coefficient measuring device 6 is displaced back to the conveyor 2 for performing friction measurements. The waste container 13 can be provided with a cleaning device 13A arranged for cleaning a discharged contact piece 11 in order to make it for reuse.

Figure 3:
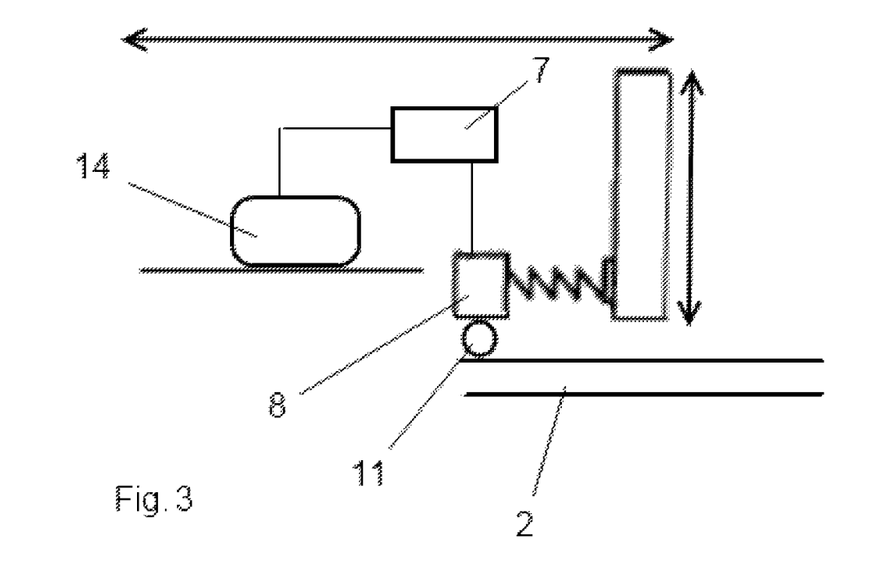
FIG. 3 very schematically shows an embodiment of a contact portion cleaning device used in a system of FIG. 1.

In FIG. 3 another embodiment of a replacement device according to the invention is shown. In this embodiment the replacement device comprises a cleaning device 14 to which the friction coefficient measuring device 6 can be displaced after a friction measurement has been effected. Under control of the control unit 7 the friction coefficient measuring device 6 is moved such that the contact piece can be positioned within the cleaning device 14 for making the contact piece 11 suitable for reuse. Dependent on the kind of cleaning device 14 used the slider 8 can be provided with a gripper for releasing the contact piece into the cleaning device and to pick a cleaned contact piece out of the cleaning device 14 after cleaning has been completed. In this regard, in the context of the present application, cleaning a used contact piece and reusing a cleaned contact piece is also considered as replacing a contact piece.

Figure 4:
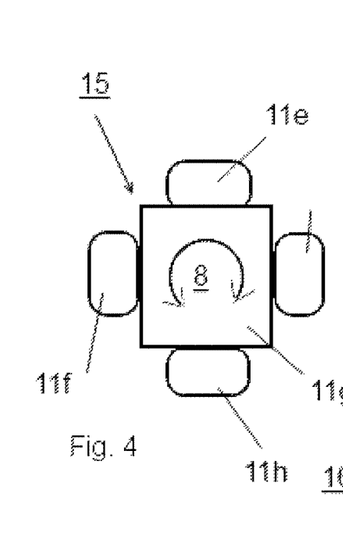
FIG. 4 very schematically shows another embodiment of a rotatable contact portion replacement device used in a system of FIG. 1.

In FIG. 4 a further embodiment of a replacement device according to the invention is shown schematically. In this embodiment the replacement device of the friction coefficient measuring device 6 comprises a displaceable magazine 15 formed by a slider 8 which is mounted as to be rotatable around an axis and which carries a plurality (in the shown embodiment four) separate contact portions 11e-11h. For replacing a contact piece 11h the control unit 7 controls the displaceable magazine 15 for moving the contact portion 11h out of contact with the conveyor surface 3 after a measuring period has ended, then the slider 8 is rotated with an angle of 90 degrees and then another contact portion e.g. 11g is moved into contact with the conveyor surface for contacting the conveyor surface 3 for performing a friction measurement. For sake of clarity only the slider and the four contact pieces are shown in FIG. 4. After all the contact pieces 11e-11h have been used they can be substituted for other contact pieces in accordance with the embodiment shown in FIG. 2 or all the contact pieces 11e-11h can be cleaned in order to make them suitable for reuse as described with reference to FIG. 3.

Figures 5, 6:
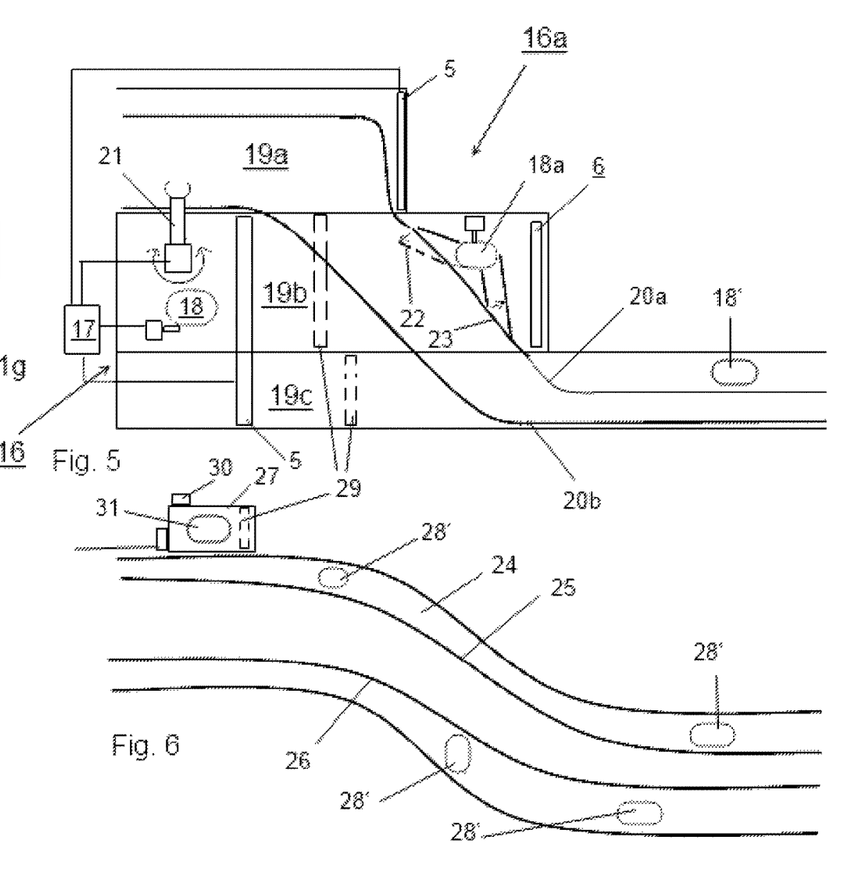
FIG. 5 very schematically shows an embodiment of a conveyor and lubricating system according to the invention comprising an item base surface friction coefficient measuring device.
FIG. 6 very schematically shows another embodiment of a conveyor and lubricating system according to the invention comprising an item base surface friction coefficient measuring device.

In FIG. 5 a further embodiment of a conveyor and lubricating system 1' according to the invention is shown in which in addition to the friction coefficient measuring device 6 an item base surface friction coefficient measuring device 16 for measuring a quantity proportional to the friction coefficient of an item base surface 4A (see FIG. 1) is provided. The item base surface friction coefficient measuring device 16 provides a signal indicative for said measured quantity proportional to the item base surface friction coefficient to control means 17 which can be separate from the control unit 7 or integrated therewith. Analogous to the friction coefficient measuring device 6 the item base surface friction coefficient measuring device 16 comprises an item base surface control unit for controlling functions and programmable operations of the item base surface friction coefficient measuring device 16 which in the shown embodiment is integrated in the control means 17. The control means 17 is arranged for controlling the lubricating dispensing device 5 for regulating the lubricant amount to be dispensed taking the measured quantity proportional to the item base surface friction coefficient into account.

The item base surface friction coefficient measuring device 16 comprises an item holder 18 and an item base surface contact portion for contacting the base surface 4A of an item 4 in order to measure the item base surface friction coefficient.

In the embodiment shown in FIG. 5 the conveyor 2 is formed by three juxtaposed conveyor components 19a, 19b, 19c. Above these conveyor components two item guides 20a, 20b are provided for guiding incoming items (at the left side of the drawing) towards an exit side (at the right side of the drawing) at which—in this embodiment—the items are transported one by one by the conveyor component 19c. The item base surface friction coefficient measuring device 16 comprises a picking up device 21 which is arranged for picking up an item transported in the conveyor path between the guides on the conveyor surface of conveyor component 19a out of the stream of transported items and into the holder 18. Here the item base surface friction coefficient is measured analogous to the manner as disclosed in WO-A-2010/063040 since the item base surface contact portion for contacting the base surface 4A of an item 4 is (part of) a conveyor. In this embodiment the conveyor track on which the item is positioned for measuring the item base surface friction coefficient, which conveyor track is also called measuring conveyor track, is formed by a part of the conveyor component 19b which is in a position outside the guides 20a, 20b and which thus does not form part of the conveyor path in which the stream of items are transported from the incoming end to the exit side. After the item base surface friction coefficient measurement is performed the picking up device 21 of the item base surface friction coefficient measuring device positions the item on which the measurement was performed back in the conveyor path on the conveyor surface between the guides 20a, 20b.

In FIG. 5 also a further embodiment of a item base surface friction coefficient measuring device 16a is indicated in which the item base surface friction coefficient measuring device 16a comprises a first switch 22 for diverting an item from the conveyor surface into the measuring conveyor track above which the holder 18a is positioned. The measuring conveyor track thus forms an isolated portion of the conveyor, meaning that this measuring conveyor track is not part of the conveyor path between the guides. After the item base surface friction coefficient measurement has been performed the item is transferred back from the measuring conveyor track in the conveyor path on the conveyor surface between the guides 20a, 20b via a second switch 23. As can be seen in FIG. 5 the switches 22, 23 are formed be swivable parts of the guide 20a. Please note that also other places of the conveyor components can be used to measure the item base surface friction component such as position 18'.

In FIG. 6 another type of conveyor is shown which in this case is a modular conveyor 24 above which the guides 25, 26 are positioned to provide a conveyor path via which items are to be transported. In this FIG. 6 an embodiment is shown in which a separate measuring conveyor track 27 is used for measuring the item base surface friction coefficient. The track surface of the measuring conveyor 27 is formed of the same material as the surface of the 24. For convenience sake only the holder 28 for holding an item to be measured is indicated. The item to be measured can be positioned on the separate measuring conveyor by using a picking up device or a switch as discussed above. The measuring conveyor track surface of this separate measuring conveyor is formed of the same material as the conveyor surface and thus has the same frictional properties. In addition or alternative to the separate measuring conveyor 27 one or more isolated portions 28' of the conveyor surface of the conveyor on which the items are transported could be appointed for measuring the item base surface friction coefficient. Preferably such measuring conveyor track is positioned near an S-shaped transfer bend of the conveyor for transporting items making diversion of an item to be measured out of the conveyor path into the measuring track more easily.

As indicated in FIGS. 5 and 6 the item base surface friction coefficient measuring device 16 comprises a measuring conveyor cleaning device 29 for cleaning the measuring conveyor track surface, which cleaning device 29 in this embodiment is positioned below the conveyor component 19b and below the separate measuring conveyor 27, respectively to clean the returning conveyor surface.

In the embodiment shown in FIG. 6 the item base surface friction coefficient measuring device comprises a weighing device 30 for weighing an item of which the item base surface friction coefficient is to be measured. The weighing device 30 is operationally connectable to the control unit to provide data indicative for the measured weight. Such data can be beneficial in regulating the lubricant amount to be dispensed in order to maintain the measured quantity proportional to the friction coefficient within a predetermined range. In particular when properly combining data relating to the measured item base surface friction coefficient, the friction coefficient of the conveyor surface and the weight the lubricant amount to be dispensed to be dispensed can be regulated as desired. Additionally in the embodiment shown in FIG. 6 the item base surface friction coefficient measuring device comprises an image obtaining and processing device 31 for obtaining an image of an item of which the item base surface friction coefficient is to be measured and for processing said obtained image. The image obtaining and processing device 31 is operationally connectable to the control unit. In this manner it is possible to determine or at least estimate the position of the center of gravity of an item to be transported with regard to the conveyor surface which position is contributory to the operation of the system and the amount of lubricant to be dispensed. E.g. are item having an center of gravity at a large distance from the conveyor surface has a greater tendency to overturn than an item of which the center of gravity is positioned close to the conveyor surface and the amount of lubricant then needs to be larger than the amount in case the center of gravity is positioned closer to the conveyor surface.

Figure 7:
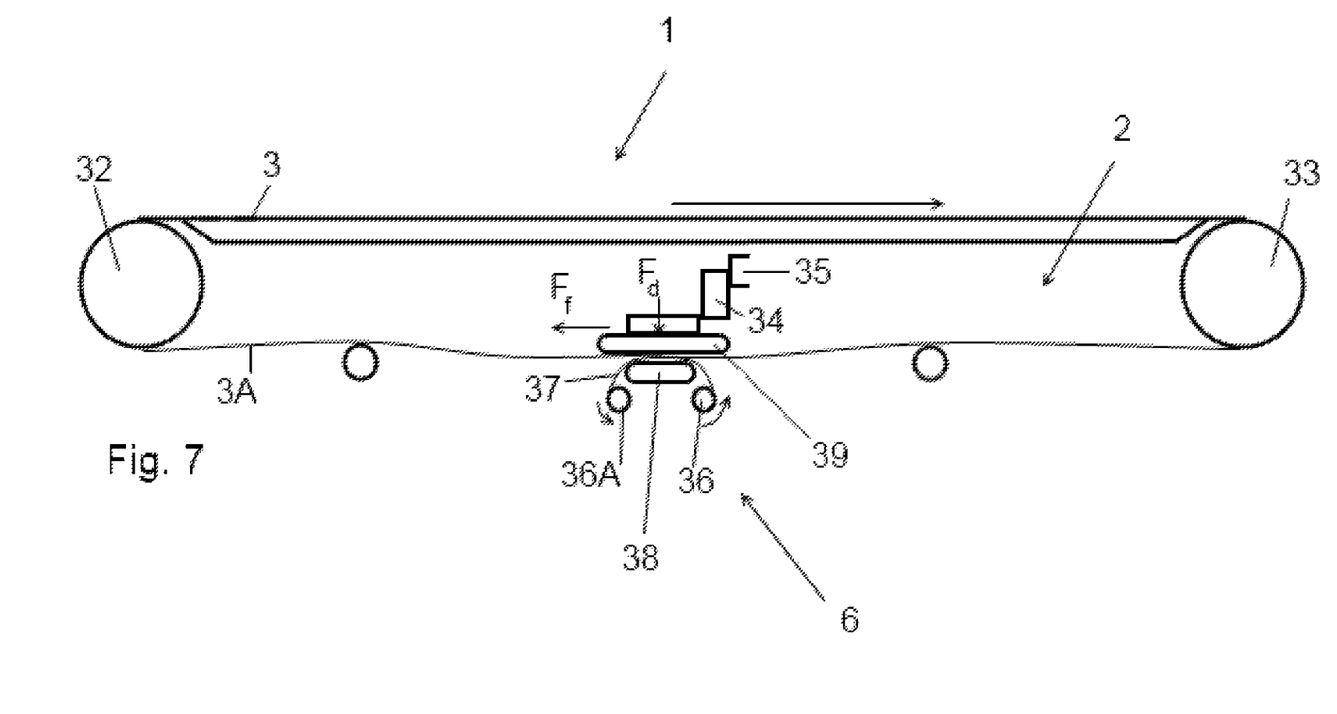
FIG. 7 very schematically shows a further embodiment of a conveyor and lubricating system according to the invention comprising a friction coefficient measuring device arranged for measuring the friction coefficient of the returning conveyor surface.

In FIG. 7 a further embodiment of a conveyor and lubricating system 1 according to the invention is shown very schematically. The conveyor 2 is an endless conveyor having an upper conveyor surface 3 on which items are to be transported and a returning conveyor surface 3A, which is identical to the upper conveyor surface 3 but directed downwards and thus can not support items to be transported. The endless conveyor 2 is wound around a reversing roller 32 and a driven reversing roller 33. The system 1 comprises a friction coefficient measuring device 6 which is arranged for measuring the friction coefficient of the returning conveyor surface 3A. In the embodiment shown in FIG. 7 the measuring conveyor track thus is formed by the returning conveyor surface, and a measurement of the friction coefficient does not interfere with the transport of items on the upper conveyor surface 3. In the embodiment shown in FIG. 7 the contact portion of the friction coefficient measuring device 6 comprises a foil supplying device 36, 36A operatively connected to the control means (not shown for sake of clarity) for supplying a contact foil 37 and an engagement pad 38—which in this embodiment is displaceably mounted relative to the returning conveyor surface 3A under control of the control means—for bringing the contact foil 37 into engagement with the returning conveyor surface 36. The foil supplying device 36, 36A comprises in this embodiment a storage roll 36 on which a storage of contact foil is wound and a used foil roll 36A, which in this embodiment is a driven roll which is operatively connected to the control means. The foil supplying device 36, 36A is arranged such that the contact foil 37 can be supplied in between the engagement pad 38 and the conveyor surface 3A. To measure the friction coefficient a predetermined force $F_d$ is applied on the side of the returning conveyor surface opposite the side at which the foil 37 engages the returning conveyor surface 3A by a pressure shoe 39 which is moved downwards under control of the control means. This pressure shoe 39 is mounted to a load cell 34 which is fixed to the stationary 'world' 35. The load cell 34 measures the force $F_f$ in transport direction and derives from this force $F_f$ the friction coefficient and sends data representing the friction coefficient to the control means which is arranged for controlling the lubricating dispensing device (not shown for sake of clarity) for regulating the lubricant amount to be dispensed in order to maintain the measured quantity proportional to the measured friction coefficient within a predetermined range. Periodically or after each measurement of the friction coefficient the pressure shoe 39 and the engagement pad 38 are—under control of the control means—moved away from each other and out of engagement with the conveyor surface after which the used foil roll 36A is rotated under control of the control means for unwinding an unused portion of contact foil from the storage roll 36, after which a new measurement of the friction coefficient can be performed.

The invention claimed is:

1. A conveyor system, said system comprising:
   a conveyor having a conveyor surface, said conveyor being arranged for transporting items along a conveyor path on the conveyor surface;
   a lubricant dispensing device dispensing a lubricant composition on the conveyor surface;
   a friction coefficient measuring device measuring a quantity proportional to the friction coefficient of said conveyor surface and providing a signal indicative for said measured quantity proportional to the friction coefficient, said friction coefficient measuring device including a contact portion and a replacement device, said contact portion contacting the conveyor surface and said replacement device automatically replacing the contact portion of the friction coefficient measuring device; and
   a control controlling said lubricant dispensing device, said measuring device being operatively connectable to said control for supplying said signal indicative for said measured quantity proportional to the friction coefficient to said control, said control controlling the lubricating dispensing device for regulating the lubricant amount to be dispensed in order to maintain the measured quantity proportional to the friction coefficient within a predetermined range.

2. A system according to claim 1, wherein said conveyor is arranged for transporting items having a base surface contacting the conveyor surface along a conveyor path; said system further including an item base surface friction coefficient measuring device for measuring a quantity proportional to the friction coefficient of said item base surface and for providing a signal indicative for said measured quantity proportional to the item base surface friction coefficient to said control, said item base surface friction coefficient measuring device including an item holder and an item base surface contact portion for contacting the base surface of an item, said item base surface friction measuring device being operatively connectable to said control for supplying said signal indicative for said measured quantity proportional to the item base surface friction coefficient to said control.

3. A system according to claim 2, wherein said control is arranged for controlling the lubricating dispensing device for regulating the lubricant amount to be dispensed taking the measured quantity proportional to the item base surface friction coefficient into account.

4. A system according to claim 2, wherein the item base surface friction coefficient measuring device includes a cleaning device cleaning an item base surface contact portion.

5. A system according to claim 2, wherein the item base surface friction coefficient measuring device is arranged for picking up an item transported along the conveyor path on the conveyor surface, and wherein the item base surface friction coefficient measuring device is arranged for measuring a quantity proportional to the friction coefficient of a base surface of an item picked up from the conveyor surface.

6. A system according to claim 4, wherein the item base surface friction coefficient measuring device is arranged for positioning an item back on the conveyor surface after the item base surface friction coefficient measuring device has performed an item base surface friction coefficient measurement.

7. A system according to claim 6, wherein the item base surface friction coefficient measuring device includes a first switch diverting an item from the conveyor path to the measuring conveyor track.

8. A system according to claim 7, wherein the item base surface friction coefficient measuring device includes a second switch conveying an item from the measuring conveyor track back in the conveyor path.

9. A system according to claim 2, wherein the item base surface contact portion for contacting the base surface of an item includes a measuring conveyor track having a measuring conveyor track surface for supporting an item, said measuring conveyor track surface being different from the conveyor path.

10. A system according to claim 9, wherein the measuring conveyor track is a measuring conveyor separate from the conveyor for transporting items.

11. A system according to claim 9, wherein the measuring conveyor track is formed by an isolated portion of the conveyor surface of the conveyor on which the items are transported.

12. A system according to claim 11, wherein the measuring conveyor track is positioned near an S-shaped transfer bend of the conveyor for transporting items.

13. A system according to claim 11, wherein the conveyor is an endless conveyor having an upper conveyor surface on which items are to be transported and a returning conveyor surface, which is identical to the upper conveyor surface but directed downwards, the measuring conveyor track being formed by the returning conveyor surface.

14. A system according to claim 2, wherein the item base surface friction coefficient measuring device includes a weighing device weighing an item of which the item base surface friction coefficient is to be measured, said weighing device being operationally connectable to said control unit.

15. A system according to claim 2, wherein the item base surface friction coefficient measuring device includes an image obtaining and processing device obtaining an image of an item of which the item base surface friction coefficient is to be measured and for processing said obtained image, said image obtaining and processing device being operationally connectable to said control unit.

16. A system according to claim 2, in which said item base surface friction coefficient measuring device includes an item holder and an item base surface contact portion for contacting the base surface of an item.

17. A system according to claim 1, in which said control provides a further signal in dependence of said signal indicative for said measured quantity proportional to the friction coefficient.

18. A conveyor system comprising:
a conveyor having a conveyor surface, said conveyor being arranged for transporting items along a conveyor path on the conveyor surface;
a friction coefficient measuring device measuring a quantity proportional to the friction coefficient of said conveyor surface and providing a signal indicative for said measured quantity proportional to the friction coefficient, said friction coefficient measuring device including a contact portion contacting the conveyor surface; and
a control operatively connectable to said measuring device for receiving said signal indicative for said measured quantity proportional to the friction coefficient, said control providing a further signal in dependence of said signal indicative for said measured quantity proportional to the friction coefficient, wherein the friction coefficient measuring device includes a replacement device automatically replacing the contact portion of the friction coefficient measuring device, and in that the control compares said measured quantity proportional to the friction coefficient indicated by said signal indicative for said measured quantity with a threshold value and for providing said further signal when said measured quantity equals to or exceeds said threshold value.

19. A system according to claim 18, wherein the friction coefficient measuring device includes a control unit controlling functions and programmable operations of the friction coefficient measuring device.

20. A system according to claim 19, wherein the control unit controls the replacement device for periodically replacing a contact portion.

21. A system according to claim 19, wherein the control unit controls the replacement device for replacing a contact portion each time new items are to be transported by said conveyor.

22. A system according to claim 19, wherein the control unit controls the replacement device for replacing the contact portion outside the measuring periods.

23. A system according to claim 22, wherein the control unit controls the replacement device replacing the contact portion each time after a measuring period has ended.

24. A system according to claim 18, wherein the contact portion is movably mounted relative to the conveyor surface, wherein the control unit controls the friction coefficient measuring device for moving a contact portion into contact with the conveyor surface for measuring a quantity proportional to the friction coefficient of said conveyor surface during measuring periods which is shorter than a transport period in which the conveyor transport items and for moving the contact portion out of contact with the conveyor surface outside the measuring period.

25. A system according to claim 24, wherein the friction coefficient measuring device includes a displaceable magazine containing a plurality of separate contact portions, said magazine being displaceable relative to the conveyor surface for allowing one contact portion of said plurality of contact portions to be movable relative to the conveyor surface for contacting the conveyor surface.

26. A system according to claim 25, wherein the control unit controls the displaceable magazine for moving said one contact portion of the plurality of contact portions out of contact with the conveyor surface after a measuring period has ended and for allowing another contact portion of said plurality of contact portions to be movable relative to the conveyor surface for contacting the conveyor surface.

27. A system according to claim 24, wherein the contact portion of the friction coefficient measuring device includes a foil supplying device supplying a contact foil and an engagement pad for bringing the contact foil into engagement with the conveyor surface, said foil supplying device being arranged for supplying contact foil in between the engagement pad and the conveyor surface.

28. A system according to claim 18, wherein a contact portion is formed by a separate disposable contact piece.

29. A system according to claim 28, wherein the friction coefficient measuring device includes a discharge conveyor discharging a contact piece to a waste container.

30. A system according to claim 18, wherein the friction coefficient measuring device includes a cleaning device cleaning the contact portion.

31. A system according to claim 30, wherein the cleaning device is arranged for cleaning a contact piece for making the contact piece suitable for reuse.

32. A system according to claim 18, including a lubricant dispensing device dispensing a lubricant composition on the conveyor surface, said control controlling the lubricating dispensing device for regulating the lubricant amount to be dispensed in order to maintain the measured quantity proportional to the friction coefficient within a predetermined range.

* * * * *

UNITED STATES PATENT AND TRADEMARK OFFICE
CERTIFICATE OF CORRECTION

PATENT NO.        : 9,592,966 B2
APPLICATION NO.   : 14/910441
DATED             : March 14, 2017
INVENTOR(S)       : Rick Wilhelmus van den Berg et al.

It is certified that error appears in the above-identified patent and that said Letters Patent is hereby corrected as shown below:

Column 2, Line 2: "band" should be --hand--
Column 5, Line 54: "IIP" should be --EP--
Column 17, Line 16: "are" should be --an--
Column 17, Line 46: "36" should be --3A--

Signed and Sealed this
Twenty-seventh Day of June, 2017

Joseph Matal
*Performing the Functions and Duties of the*
*Under Secretary of Commerce for Intellectual Property and*
*Director of the United States Patent and Trademark Office*